United States Patent [19]
Wakimura et al.

[11] Patent Number: 5,959,142
[45] Date of Patent: Sep. 28, 1999

[54] PROCESS FOR REFINING METHACRYLIC ACID

[75] Inventors: Kazuo Wakimura; Tadaharu Hase; Yoshihiro Sezaki; Koji Fujita; Takeshi Isobe, all of Osaka-fu; Shin-ichi Tadokoro; Rensuke Ikarashi, both of Niigata-ken, all of Japan

[73] Assignees: Mitsui Chemicals, Inc., Tokyo; Kuraray Co., Ltd., Okayama-ken, both of Japan

[21] Appl. No.: 08/550,801

[22] Filed: Oct. 31, 1995

[30] Foreign Application Priority Data

Nov. 4, 1994 [JP] Japan ................................. 6-270826

[51] Int. Cl.$^6$ ................................................. C07C 51/16
[52] U.S. Cl. .......................... 562/532; 562/538; 562/545; 562/600
[58] Field of Search ................................. 562/532, 538, 562/545, 600

[56] References Cited

U.S. PATENT DOCUMENTS 4,533,750   8/1985   Matsumura et al. ..................... 562/600

FOREIGN PATENT DOCUMENTS

| 0376117 | 7/1990 | European Pat. Off. |
| 1084487 | 1/1955 | France |
| 862887 | 11/1952 | Germany |
| 997325 | 7/1965 | United Kingdom |

*Primary Examiner*—Gary Geist
*Assistant Examiner*—Sreeni Padmanabhan
*Attorney, Agent, or Firm*—Burns, Doane, Swecker & Mathis, L.L.P.

[57] ABSTRACT

A process for producing refined methacrylic acid comprising the steps of oxidizing methacrolein and the like catalytically in a vapor phase to form a methacrylic acid-containing gas, cooling and condensing the gas to an aqueous methacrylic acid solution, adding to the solution an organic solvent that forms two liquid phases with water to carry out an extraction operation and thereby to obtain an extract, bringing the extract into contact with water to mix them together, separating the mixture into an organic phase and a water phase, and distilling the organic phase. According to this process, highly refined methacrylic acid containing little dibasic acids such as maleic acid and citraconic acid can be obtained economically and without increasing wastes that are unrecoverable to the process.

5 Claims, No Drawings

PROCESS FOR REFINING METHACRYLIC ACID

BACKGROUND OF THE INVENTION

1. Field of the Invention

The present invention relates to a process for producing highly refined methacrylic acid containing little dibasic acids such as maleic acid and citraconic acid efficiently on an industrial scale from an aqueous methacrylic acid solution obtained by cooling a methacrylic acid-containing reaction gas formed by oxidizing methacrolein, isobutyl aldehyde, t-butanol or isobutylene catalytically in a vapor phase.

2. Description of the Related Art

Methacrylic acid is generally refined by extracting it from an aqueous methacrylic acid solution, which is obtained by cooling and condensing a methacrylic acid-containing gas formed by oxidizing a 4 C compound such as methacrolein, isobutyl aldehyde, t-butanol or isobutylene catalytically in a vapor phase, with an organic solvent, which does not mix with water and hence forms separated phases with the condensed aqueous solution, followed by distillation of the extract. The organic solvent used for this purpose may include, for example, aliphatic hydrocarbons having 5 to 9 carbon atoms, aromatic hydrocarbons such as benzene and tolunene and esters such as methyl methacrylate.

The process for producing methacrylic acid by the catalytic oxidation of the above-described 4 C compounds in one or two reaction stages or more is now actually practiced on an industrial scale. However, a variety of side reactions occur simultaneously in the catalytic oxidation reaction and therefore the reaction product gas contains a variety of by-produced impurities in addition to the desired methacrylic acid. The miscellaneous by-produced impurities get mixed partially in the aqueous methacrylic acid solution obtained by cooling and condensing the reaction product gas and in the extract from the aforesaid aqueous solution with the organic solvent. The principal by-produced impurities include acetaldehyde, acetone, acetic acid, acrolein, methacrolein, acrylic acid, maleic acid, citraconic acid, aromatic aldehydes, aromatic carboxylic acids, heterocyclic compounds and the like.

Among these by-produced impurities, acetaldehyde, acetone, acetic acid, acrolein and methacrolein, which are lower boiling point components than methacrylic acid, can be separated by distillation, and aromatic compounds, higher boiling point components, can also be separated by distillation. However, it is difficult to separate by distillation dibasic acids such as maleic acid and citraconic acid transferred to the extract phase along with methacrylic acid during the extraction.

With a view to removing these hardly separable impurities from methacrylic acid, the present inventors have examined a process in which the impurities-containing methacrylic acid extract prior to the distillation is brought into contact with a basic ion-exchange resin, followed by refining of the resultant extract by distillation. Thus, inventions of U.S. Pat. No. 4,879,412 and Japanese Patent Laid-Open No. 193740/1989 have been proposed. The present inventors have also studied a process in which the impurities-containing methacrylic acid extract prior to the distillation is brought into contact with a basic amine, followed by refining of the resultant extract by distillation. As a result, an invention of U.S. Pat. No. 5,196,578 has been proposed.

According to the processes proposed by the inventors, it has been proved that impurities including dibasic acids such as maleic acid contained in methacrylic acid are adsorbed or made high boiling point components by bringing the methacrylic acid extract into contact with a basic ion-exchange resin or a basic amine, and the extract thus treated is subjected to the subsequent distillation step to produce methacrylic acid of a high quality.

To solve the aforementioned problems, in processes other than those proposed by the present inventors, for example, in the specification of Japanese Patent Laid-Open No. 152438/1985, there is proposed a process comprising the steps of subjecting an aqueous methacrylic acid solution obtained by cooling and condensing the reaction product gas to an evaporation step such as distillation to remove low boiling point components, extracting methacrylic acid from the resulting solution with an organic solvent that forms an azeotropic composition with water, such as an aromatic hydrocarbon, bringing the extract into contact with an aqueous hydrogensulfite solution to separate the mixture thus obtained into two phases, and subjecting only the oily phase to a distillation and refining step. Further, for example, in the specification of Japanese Patent Laid-Open No. 178842/1985, there is proposed a process comprising the steps of cooling and condensing the reaction product gas to an aqueous methacrylic acid solution, extracting methacrylic acid from the aqueous solution with an aromatic or aliphatic hydrocarbon solvent, and adding an alkali or an aqueous hydrazine solution to the extract to separate maleic acid and the like as a salt by precipitation.

In these conventional processes, however, substances, which do not originally exist in their process solutions, are incorporated so that waste water and wastes, which are unrecoverable to and unreusable in the processes, are evolved therein to render the processes defective. Therefore, expenses are necessary to treat the waste water and wastes that are unrecoverable to and unreusable in the processes. Consequently, the processes involve an essential problem of deteriorated economical efficiency.

Further, a reaction of polymerizing methacrylic acid takes place due to the substances incorporated, giving rise to the problem of equipment being contaminated.

SUMMARY OF THE INVENTION

It is an object of the present invention to provide a process for refining methacrylic acid for the purpose of producing highly refined methacrylic acid at low cost by reducing the amount of impurities including dibasic acids such as maleic acid and citraconic acid.

The present inventors have intensively investigated a process which removes the above-described dibasic acids such as maleic acid and citraconic acid efficiently, does not evolve waste water and wastes which are unrecoverable to the process, and is excellent in economical efficiency. As a result, it has been found that the contents of dibasic acids such as maleic acid and citraconic acid can be decreased to significantly low concentrations by adding a small amount of water, and the added water can be recovered and reused in the process by separating it from the methacrylic acid extract. The present invention has been completed on the basis of this finding.

Thus, the present invention provides a process for refining methacrylic acid comprising the steps of:

oxidizing methacrolein, isobutyl aldehyde, t-butanol or isobutylene catalytically in a vapor phase to form a methacrylic acid-containing reaction gas;

cooling and condensing the reaction gas to an aqueous methacrylic acid solution;

adding to the aqueous solution an organic solvent that forms two liquid phases with water to carry out an extraction operation and thereby to obtain an extract of the methacrylic acid in the organic solvent;

bringing the extract into contact with water;

separating the resultant mixture into an organic phase and a water phase; and distilling the organic phase for refining.

According to the present invention, it is possible to remove dibasic acids such as maleic acid and citraconic acid to a considerably low level prior to the distillation and refining, and thereby provide highly refined methacrylic acid containing little dibasic acids, economically and without increasing the amount of wastes from the process.

DETAILED DESCRIPTION OF THE PREFERRED EMBODIMENTS

The present invention will be described in detail hereunder.

When methacrolein, isobutyl aldehyde, t-butanol or isobutylene is oxidized in a vapor phase in one or more stages of reaction using a catalyst for catalytic oxidation composed primarily of molybdenum oxide or a composite oxide thereof, a reaction product gas containing methacrylic acid as a main component can be obtained. The product gas is cooled and condensed to an aqueous methacrylic acid solution and the condensed aqueous solution is extracted with a given organic solvent to obtain a methacrylic acid extract. The organic solvent useful in the practice of the present invention is a conventionally known organic solvent which does not mix with water to cause phase separation, i.e., forming two liquid phases with water. The exemplary suitable organic solvents include specifically aliphatic hydrocarbons having 5 to 9 carbon atoms, aromatic hydrocarbons such as benzene and toluene, and esters such as methyl methacrylate. They may be used alone or as a mixture.

In the present invention, water is added to the methacrylic acid extract, and they are fully mixed and brought into contact with each other to subject the mixture to extraction again. Thus, dibasic acids such as maleic acid and citraconic acid in the extract are transferred to the water phase and thereby separated and removed from the organic phase. The organic phase is sent to a distillation step where methacrylic acid is obtained as the product. The water phase may be preferably reused as a process water by recycling and mixing it to the aqueous methacrylic acid solution obtained by cooling and condensing thus obtained methacrylic acid-containing reaction gas, but it may also be subjected to distillation together with the organic phase or discharged as waste water.

As the water specified by the present invention, it is common to use distilled water or ion-exchanged water not containing metal salts and the like, but is also possible to use potable water or water with methacrylic acid dissolved.

The amount of the water added is suitably in the range of from 0.01 to 10% by weight, preferably from 0.1 to 5% by weight, relative to the extract.

To add and mix the water with the extract, generally, both liquids are fully brought into contact with each other by mixing in a continuous or batch stirring vessel or in a line mixer and sent to a filter-type or settling-type two-phase separation vessel. Also, it is possible to use a packing-type or spray-type extraction column or an orifice column-type extraction column. Here, the organic phase is preferably fed to the distillation step in the state under which the water phase and the organic phase are completely separated into two phases. The organic phase with water droplets mixed may also be fed to the distillation step.

The time for mixing and contacting the extract with water is suitably from 10 seconds to 1 hour, preferably from 30 seconds to 10 minutes. The contact temperature is not particularly restricted and is commonly in the range of from 0° to 100° C.

After mixing and contact with the water, the extract is allowed to stand to separate the mixture into two phases. The time required for this operation is suitably from 30 seconds to 2 hours.

In all the operations after obtaining the condensed solution, no particular restrictions are placed on the operation pressures, which are usually atmospheric.

The present invention will be illustrated specifically by the following examples. However, the present invention shall not be limited to or by these examples.

EXAMPLE 1

Using a molybdenum-base composite oxide catalyst as a former-stage oxidation catalyst and a molybdenum-base heteropoly-acid catalyst as a latter-stage catalyst, isobutylene was oxidized to form a reaction product gas, which was cooled and condensed to an aqueous methacrylic acid solution. Then, low boiling point components such as acetone and methacrolein were removed from the aqueous solution, and methacrylic acid was extracted from the resulting aqueous solution with n-heptane as an extraction solvent to obtain an extract. The extract comprised 18.8% by weight of methacrylic acid, 0.16% by weight of water, 35 ppm by weight of maleic acid, 60 ppm by weight of citraconic acid, a small amount of other impurities, and n-heptane as the rest.

Seventy five grams of the extract was mixed with 1.5 g of distilled water, and the mixture was stirred at 25° C. for two minutes and allowed to stand for one minute to clarify the liquid mixture. Then, the supernatant liquid was separated.

The composition of the liquid thus separated was 18.7% by weight of methacrylic acid, 0.17% by weight of water, 2.1 ppm by weight of maleic acid, 16 ppm by weight of citraconic acid and a trace amount of other impurities, the rest being n-heptane. Here, the rate of removal of maleic acid was 94%, while that of citraconic acid was 73.3 %.

Phenothiazine (100 ppm by weight) was added as a polymerization inhibitor to the supernatant liquid obtained above, and the mixture was distilled to obtain refined methacrylic acid.

Five grams of the refined liquid was taken in a 10-cc test tube, to which 100 ppm by weight of phenothiazine was added as a polymerization inhibitor. The test tube was tightly sealed with air enclosed and heated to 120° C. to carry out a polymer deposition test. As a result, the time for depositing a polymer was found to be 6 hours.

Comparative Example 1

Refined methacrylic acid was prepared by distilling the extract obtained in Example 1 in the same manner as in Example 1, except that distilled water was not added to and mixed with the extract. Then, a polymer deposition test was carried out for the refined liquid in the same manner as in Example 1. The time for depositing a polymer was found to be 4 hours and 20 minutes.

EXAMPLE 2

Three grams of distilled water was added to and mixed with 75 g of the same extract as prepared in Example 1, and the mixture was stirred at 25° C. for two minutes and allowed to stand for one minute. Then, the supernatant liquid was separated.

The liquid thus separated was composed of 18.8% by weight of methacrylic acid, 0.18% by weight of water, 1 ppm by weight of maleic acid, 13 ppm by weight of citraconic acid, a trace amount of other impurities, and n-heptane as the rest. Here, the rate of removal of maleic acid was 97%, while that of citraconic acid was 78.3%.

The supernatant liquid obtained above was distilled in the same manner as in Example 1 to obtain a refined liquid, and a polymer deposition test was carried out for the refined liquid in the same manner as in Example 1. It took 7 hours and 40 minutes to deposit a polymer.

EXAMPLE 3

A supernatant liquid was obtained in the same manner as in Example 1, except that the standing time after the addition and mixing of distilled water was changed to 30 seconds.

The liquid so obtained was composed of 18.7% by weight of methacrylic acid, 0.17% by weight of water, 16 ppm by weight of maleic acid, 28 ppm by weight of citraconic acid, a trace amount of other impurities, and n-heptane as the rest. Here, the rate of removal of maleic acid was 51.5%, while that of citraconic acid was 53.5%.

The supernatant liquid obtained above was distilled in the same manner as in Example 1 to obtain a refined liquid, and a polymer deposition test was carried out for the refined liquid in the same manner as in Example 1. It took 5 hours and half to deposit a polymer.

EXAMPLE 4

Distilled water was added at a rate of 2 kg/hr to an extract fed at a rate of 100 kg/hr, which comprised 19.4% by weight of methacrylic acid, 0.17% by weight of water, 14 ppm by weight of maleic acid, 22 ppm by weight of citraconic acid, a small amount of other impurities, and n-heptane as the rest. Both liquids were mixed in a static mixer and fed to a continuous extraction vessel operated at 10 kg/cm$^2$ gauge, where the organic phase was discharged at the top at a rate of 100 kg/hr and the water phase at the bottom at a rate of 2 kg/hr.

The static mixer employed had an inner diameter of 4 inches and comprised six elements. The extraction vessel was of a filter-type and had a shell diameter of 250 mm and a shell height of 450 mm.

The organic phase obtained was composed of 19.3% by weight of methacrylic acid, 0.15% by weight of water, 0.9 ppm by weight of maleic acid, 3 ppm by weight of citraconic acid, a small amount of other impurities, and n-heptane as the rest. Here, the rate of removal of maleic acid was 93.6%, while that of citraconic acid was 86.4 %.

The organic phase obtained above was distilled to obtain a refined liquid, and a polymer deposition test was carried out for the refined liquid in the same manner as in Example 1. The time for depositing a polymer was 8 hours.

What is claimed is:

1. A process for refining methacrylic acid comprising the steps of:

oxidizing methacrolein, isobutyl aldehyde, t-butanol or isobutylene catalytically in a vapor phase to form a methacrylic acid-containing reaction gas;

cooling and condensing the reaction gas to form an aqueous methacrylic acid solution;

adding to the aqueous solution an organic solvent which forms two liquid phases with water to carry out an extraction operation and thereby to obtain an extract of the methacrylic acid in the organic solvent;

bringing the extract into contact with water in an amount of from 0.01 to 10% by weight relative to the extract to selectively remove dibasic acids therefrom;

separating the resultant mixture into an organic phase and a water phase; and distilling the organic phase.

2. The process according to claim 1, wherein the organic solvent is an aliphatic hydrocarbon having from 5 to 9 carbon atoms, an aromatic hydrocarbon, an ester or a mixture thereof.

3. The process according to claim 1, wherein the organic solvent is n-heptane, benzene or toluene.

4. The process according to claim 1, wherein the water phase after being brought into contact with the extract is reused as a process water.

5. The process according to claim 1, wherein the water phase after being brought into contact with the extract is recycled and mixed to the aqueous methacrylic acid solution obtained by cooling and condensing the obtained methacrylic acid-containing reaction gas.

* * * * *